United States Patent [19]

Nelson

[11] 4,301,294
[45] Nov. 17, 1981

[54] 16-PHENOXY PGE$_2$ COMPOUNDS

[75] Inventor: Norman A. Nelson, Galesburg, Mich.

[73] Assignee: The Upjohn Company, Kalamazoo, Mich.

[21] Appl. No.: 218,140

[22] Filed: Dec. 19, 1980

Related U.S. Application Data

[62] Division of Ser. No. 426,058, Dec. 19, 1973, which is a division of Ser. No. 252,030, May 10, 1972.

[51] Int. Cl.$^3$ ............................................. C07C 117/00
[52] U.S. Cl. .................................... 560/53; 562/463; 260/408; 260/405.5; 260/410; 260/410.5; 260/410.6
[58] Field of Search ......................... 560/53; 562/463; 260/405.5, 408, 410, 410.5, 410.6, 410.9 R

[56] References Cited
PUBLICATIONS

Kirton, B. B. et al., Proceedings of the Society for Experimental Biology and Medicine, vol. 33, No. 1, pp. 314–316, Jan. 1970.

Primary Examiner—Paul J. Killos
Attorney, Agent, or Firm—Robert A. Armitage

[57] ABSTRACT

Prostaglandin-type compounds with a phenoxy or substituted-phenoxy substituent at the C-16 position are disclosed, with processes for making them. These compounds are useful for a variety of pharmacological purposes, including anti-ulcer, inhibition of platelet aggregation, increase of nasal patency, labor inducement at term, and wound healing.

8 Claims, No Drawings

16-PHENOXY PGE$_2$ COMPOUNDS

The present application is a divisional application of Ser. No. 426,058, filed Dec. 19, 1973, now pending which is a division of Ser. No. 252,030 filed May 10, 1972.

United States Ser. No. 766,010, filed Feb. 7, 1977, now U.S. Pat. No. 4,166,988, is also a divisional application of Ser. No. 426,048. The present invention relates to prostaglandin analogs for which the essential material constituting a disclosure therefor is incorporated by reference here from U.S. Pat. No. 4,116,988.

I claim:

1. An optically active compound of the formula

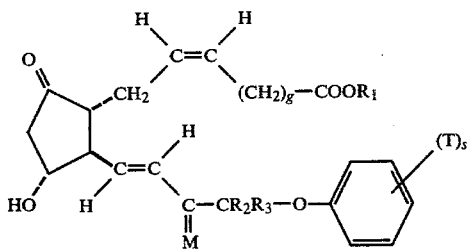

or a racemic compound of that formula and the mirror immage thereof, wherein g is an integer from 2 to 5, inclusive;
wherein M is $\alpha$-OH:$\beta$-H or $\beta$-OH:$\alpha$-H;
wherein R$_1$ is hydrogen or alkyl of one to 12 carbon atoms, inclusive, cycloalkyl of 3 to 10 carbon atoms, inclusive, aralkyl of 7 to 12 carbon atoms, inclusive, phenyl, or phenyl substituted with one, 2, or 3 chloro or alkyl of one to 4 carbon atoms, inclusive;
wherein R$_2$ and R$_3$ are hydrogen, methyl, or ethyl;
wherein T is alkyl of one to 3 carbon atoms, inclusive, fluoro, chloro, trifluoromethyl, or —OR$_4$, wherein R$_4$ is alkyl of one to 3 carbon atoms, inclusive, and
wherein s is zero, one, 2, or 3, with the proviso that not more than two T's are other than alkyl, including the lower alkanoates thereof, and the pharmacologically acceptable salts thereof when R$_1$ is hydrogen.

2. A compound according to claim 1 wherein g is 3.
3. A compound according to claim 2 wherein M is $\alpha$-OH:$\beta$-H.
4. A compound according to claim 3 wherein R$_2$ and R$_3$ are hydrogen, and is zero.
5. 16-Phenoxy-17,18,19,20-tetranor-PGE$_2$, methyl ester, an optically active compound according to claim 4 wherein R$_1$ is methyl.
6. A compound according to claim 3 wherein R$_2$ and R$_3$ are methyl, and s is zero.
7. 16-Methyl-16-phenoxy-18,19,20-trinor-PGE$_2$, an optically active compound according to claim 6 wherein R$_1$ is hydrogen.
8. 16-Methyl-16-phenoxy-18,19,20-trinor-PGE$_2$, methyl ester, an optically active compound according to claim 6 wherein R$_1$ is methyl.

UNITED STATES PATENT OFFICE
CERTIFICATE OF CORRECTION

Patent No. 4,301,294      Dated 17 November 1981

Inventor(s) Norman A. Nelson

It is certified that error appears in the above-identified patent and that said Letters Patent are hereby corrected as shown below:

Column 1, line 10
    --U.S. Pat. No. 4,166,988, is-- should read -- U.S. Pat. No. 4,116,988, is--

Column 2, line 20
    --hydrogen, and is zero.-- should read --hydrogen, and s is zero.--

Signed and Sealed this

Third Day of August 1982

[SEAL]

Attest:

Attesting Officer

GERALD J. MOSSINGHOFF

Commissioner of Patents and Trademarks